Figure 1:
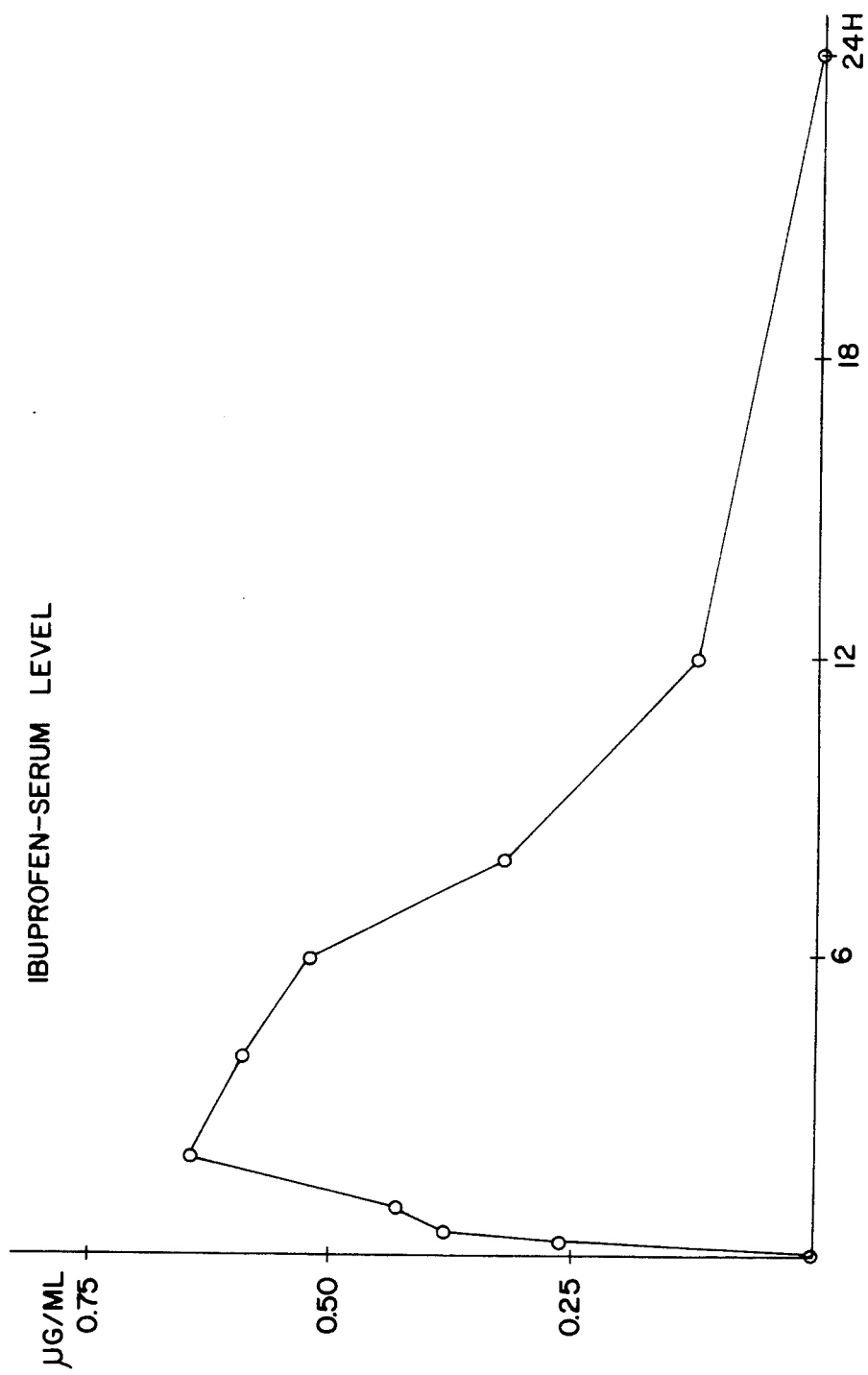

United States Patent [19]

Gruber et al.

[11] Patent Number: 4,555,524
[45] Date of Patent: Nov. 26, 1985

[54] TRANSDERMAL 2-(4-ISOBUTYLPHENYL)-PROPIONIC ACID MEDICATION AND METHODS

[75] Inventors: Klaus Gruber, Remagen; Manfred Löhner; Klaus Posselt, both of Bonn; Hans H. Wagener, Meckenheim, all of Fed. Rep. of Germany

[73] Assignee: Dolorgiet GmbH & Co KG, Bonn, Fed. Rep. of Germany

[21] Appl. No.: 443,903

[22] Filed: Nov. 23, 1981

[30] Foreign Application Priority Data

Feb. 16, 1982 [DE] Fed. Rep. of Germany ....... 3205504

[51] Int. Cl.$^4$ .............................................. A61K 31/19
[52] U.S. Cl. .................... 514/570; 514/786; 514/947
[58] Field of Search ............................ 424/317, 28, 19

[56] References Cited

U.S. PATENT DOCUMENTS 4,282,216  8/1981  Rovee et al. ......................... 424/240
4,390,520  6/1983  Nagai et al. ........................... 424/28

FOREIGN PATENT DOCUMENTS 0063870  11/1982  European Pat. Off. .

OTHER PUBLICATIONS

Farmaceutico, 1982, A–108.
Boll. Chim. Farm., 119 (1980), p. 738, G. Bramati et al., "Release Drugs in Vitro from Different Dermatological Preparations".
Patent Abstracts of Japan, vol. 6, No. 7, 1/16/82, Nissan Kagaku Kogyo K.K., "Ketoprofen Composition for Rectum Administration".
Patent Abstracts of Japan, vol. 6, No. 250, 12/9/82, Kouwa Yakuhin Kogyo K.K., "Preparation of Ibuprofen Pharmaceutical".

*Primary Examiner*—Frederick E. Waddell
*Attorney, Agent, or Firm*—Wegner & Bretschneider

[57] ABSTRACT

An externally administrable pharmaceutical which contains an effective amount of 2-(4-isobutylphenyl)propionic acid in a base is obtained by drug dissolution in a mixture of $C_{6-12}$ carboxylic acid triglycerides, glycerol monostearate-polyoxyethylene stearate mixture and polyoxyethylene-fatty acid esters. A cream is obtained by stirring this solution with an aqueous phase in the presence of heat.

6 Claims, 1 Drawing Figure

TRANSDERMAL 2-(4-ISOBUTYLPHENYL)-PROPIONIC ACID MEDICATION AND METHODS

SUMMARY OF THE INVENTION

In accordance with a first aspect of the present invention there is provided a transdermal medicament for the delivery of 2-(4-isobutylphenyl)-propionic acid (ibuprofen) to a patient which comprises a sustained release vehicle containing a pharmaceutically effective amount of 2-(4-isobutylphenyl)-propionic acid, said sustained release vehicle comprising a base capable of substantially dissolving all of said 2-(4-isobutylphenyl)-propionic acid and containing from about 30 to about 50 parts by weight $C_{6-12}$ carboxylic acid triglyceride, about 4 to about 10 parts by weight glycerol monostearate-polyoxyethylene stearate mixture and about 2 to about 10 parts by weight polyoxyethylene fatty acid ester. The transdermal medication of the present invention may be in a form suitable for transdermal application, such as in the form of a cream, ointment or gel, or in the form of a bandage having a reservoir containing the transdermal medication in a suitable form. In a preferred embodiment, the transdermal medication is provided in the form of a cream, the cream having an aqueous phase in addition to the base including the above-recited components. In such a cream, the aqueous phase preferably comprises from about 2 to about 10 parts by weight 1,2-propanediol, about 0.1 to about 1 part by weight 4-hydroxybenzoic acid methyl ester, and from about 0.1 to about 1 part by weight xanthan gum. In accordance with a second aspect of the present invention there is provided a method of topically providing an analgesic effect to a patient suffering from a localized pain which comprises topically administering to said patient the transdermal medicament.

In accordance with a third aspect of the present invention there is provided a method of topically providing an antirheumatic effect to a patient suffering from rheumatism, which comprises topically administering to said patient the transdermal medicament.

In accordance with a fourth aspect of the present invention there is provided a method of systemically administering 2-(4-isobutylphenyl)-propionic acid to a patient without a first-pass effect which comprises transdermally administering 2-(4-isobutylphenyl)-propionic acid contained in the transdermal medication, whereby a systemic effect of 2-(4-isobutylphenyl)-propionic acid is delivered to said patient without passage of 2-(4-isobutylphenyl)-propionic acid through the liver of said patient prior to delivery to the bloodstream.

DETAILED DESCRIPTION OF THE INVENTION 2-(4-isobutylphenyl)-propionic acid is a known pharmaceutical which is widely used as an antirheumatic-/antiphlogistic and analgesic predominantly in cases of degenerative and inflammatory articular diseases and in soft tissue rheumatism. Currently, it is preferred to administer 2-(4-isobutylphenyl)-propionic acid in the form of coated tablets and suppositories. Oral administration, as well as rectal administration, in case of systemically active pharmaceuticals such as 2-(4-isobutylphenyl)-propionic acid, have disadvantageous effects such as gastrointestinal disturbances, vertigo, nausea, and headache. In the case of patients suffering from gastric and duodenal ulcers, an oral administration of 2-(4-isobutylphenyl)-propionic acid is excluded.

In the case of topical administration, a pharmaceutical reaches the target organ directly while bypassing the first-pass effect, i.e., the first metabolization in the liver, this first-pass effect is unavoidable in the case of oral or rectal administration. It is possible in this manner to reduce the disadvantages encountered in case of oral and rectal administration.

For topical administration, an active ingredient must be incorporated into, for example, a cream, an ointment or a gel. It is not possible to prepare an 2-(4-isobutylphenyl)-propionic acid cream by conventional cream preparation methods because 2-(4-isobutylphenyl)-propionic acid is only sparingly soluble in water and conventional media. Attempts to prepare such a cream were obviously made in the past. For example, examination of a commercially available 10% 2-(4-isobutylphenyl)-propionic acid cream (L'Informatore Farmaceutico, 1981, A-107) under the microscope showed that the active ingredient is present in this cream in largely undissolved state in the form of fine acicular crystals. However, this cream has not found wide application up to the present. The reason can be seen in the fact that a topically administered pharmaceutical can only have a good and rapid activity if the active ingredient penetrates correspondingly through the skin. This requires the presence of a dissolved active ingredient.

It is an object of the invention to provide an externally administrable pharmaceutical which contains an effective amount of 2-(4-isobutylphenyl)-propionic acid in a base. This object is accomplished by dissolving 2-(4-isobutylphenyl)-propionic acid in a mixture of $C_6$-$C_{12}$ carboxylic acid triglycerides, glycerol monostearate-polyoxyethylene stearate mixture and polyoxyethylene fatty acid ester. The solution can be further processed in a manner known per se by use of further additives to form a cream, an ointment or a gel. Preferably a cream is prepared from this solution. Additives such as 1,2-propanediol, preserving agents such as 4-hydroxybenzoic acid methyl ester, e.g. as sodium salt, and thickening agents such as xanthan gum may be added to the aqueous phase of the cream.

As a pharmaceutically acceptable amount may be mentioned an amount sufficient to provide sufficient 2-(4-isobutylphenyl)-propionic acid for the desired pharmaceutical effect. In a preferred embodiment the non-aqueous phase contains from about 2 to about 12 parts by weight 2-(4-isobutylphenyl)-propionic acid, and in a still more preferred embodiment an amount of from about 4 to about 8 parts by weight (the part by weight in each case being calculated based upon 100 parts by weight of the total amount of the base).

As the $C_{6-12}$ carboxylic acid triglyceride component ("medium chain" triglycerides) of the base may be mentioned the caproic, caprylic, capric or lauric acid triglycerides, such as "caprylic/capric triglyceride" (Miglyol ® 812, Dynamit Nobel AG, West Germany).

The polyoxyethylene-fatty acid ester preferably contains esters of $C_{12-18}$ carboxylic acids, with a representative carboxylic acid being myristic acid or palmitic acid. The ethylene oxide units of the polyoxyethyl radical may vary between about 6 and about 100, and preferably may be from about 8 to about 12 (Arlatone ® 983, Atlas Chemical Industries).

A suitable example of a glycerol monostearatepolyoxyethylene stearate mixture may be Arlacel ® 165 (Atlas Chemical Industries).

In the transdermal medicament cream of the present invention, the aqueous phase is present in an amount of from about 40 to about 60 parts by weight of 100 parts by weight of the base.

As ingredients which are contemplated as being within the scope of the present invention may be mentioned surfactants, solvents, binding agents, preservatives and perfumes.

In a preferred embodiment of the present invention, the amounts by weight of the components are as follows:

| | |
|---|---|
| 2-(4-isobutylphenyl)-propionic acid | 4.0–5.5 g. |
| $C_{6-12}$ carboxylic acid triglycerides | 35.0–42.0 g. |
| Glycerol monostearate-polyoxyethylene stearate mixture | 6.0–8.0 g. |
| Polyoxyethylene fatty acid ester | 4.0–6.0 g. |
| 1,2-Propanediol | 4.0–6.0 g. |
| 4-Hydroxybenzoic acid methyl ester-sodium | 0.1–0.4 g. |
| Xanthan gum | 0.2–0.5 g. |
| Water q.s. to make | 100.0 g. |

The following nonlimiting examples serve to further illustrate the invention:

EXAMPLE I

A base containing 2-(4-isobutylphenyl)-propionic acid is prepared in the following manner: 42.00 g of $C_{6-12}$ carboxylic acid triglycerides (Miglyol® 812, Dynamit Nobel AG), 7.80 g of glycerol monostearatepolyoxyethylene mixture (Arlacel® 165, Atlas Chemical Industries) and 5.20 g of polyoxyethylene fatty acid ester (Arlatone® 983, Atlas Chemical Industries) are heated at a temperature of 60°–65° C. With appropriate stirring, there is dissolved into this mixture 5.00 g 2-(4-isobutylphenyl)-propionic acid, until essentially all of the acidular 2-(4-isobutylphenyl)-propionic acid has been dissolved.

An aqueous phase is prepared by mixing together 5.00 g 1,2-propanediol, 0.15 g 4-hydroxybenzoic acid methyl ester (sodium salt), 0.40 g xanthan gum and 34.45 g water. This mixture is heated to a temperature of 60°–65° C., and this aqueous phase is then added in portions to the base under conditions of stirring. After addition of the last portion of the aqueous phase, the batch is uniformly stirred until it has cooled to room temperature.

EXAMPLE II

Male Sprague-Dawley rats, each having a body weight of 80 to 100 grams were shaved on the back. Edema was initiated by subplantar injection of 0.1 ml of a 1% carrageenan solution into the left hind paw. Thirty minutes after the injection, an amount of cream corresponding to 100 mgs./kg. of body weight of 2-(4-isobutylphenyl)-propionic acid was administered by inunction at the shaved back of the animals. The inuncted surface area was 15 to 20 sq.cm. in each case. Immediately after the injection and then in intervals of 15 hours each after the inunction, the volumes of the paws were determined. The degree of inhibition of the edema was determined in comparison with a control group (n=54 animals) which was not treated with cream.

Table 1, below, shows that the inhibitory effect occurs substantially sooner when using the cream according to the invention and that the overall effect is higher than in case of the commercially available product.

TABLE 1

| | Degree of Edema Inhibition in Percent After | | | | |
|---|---|---|---|---|---|
| | 1 hrs. | 2 hrs. | 3 hrs. | 4 hrs. | 5 hrs. |
| Cream according to the invention (n = 12 animals) | 76 | 81 | 81 | 73 | 66 |
| Commercially available product (n = 36 animals) | 29 | 53 | 53 | 50 | 44 |

EXAMPLE III

Clinical Examination

In an openly controlled study carried out in randomized manner, the cream according to the invention and the commercially available cream were examined for their effectiveness. A total of 14 patients suffering from a shoulder-arm syndrome were treated, each treatment group comprising 7 patients after derandomization. A 5 to 10 cm. cord of each was applied 3 to 4 times per day to the painful region and rubbed into the skin on a large surface area. The pain at rest, in motion and on compression as well as the restriction of motion and the firmness of grip were evaluated before and after the three day regimen. As seen from Table 2, a more favorable therapeutic result was achieved with the cream according to the invention despite the fact that only half the amount of 2-(4-isobutylphenyl)-propionic acid was applied, as compared with the commercially available cream. Moreover, all of the patients rejected a further treatment with the commercially available cream because it is poor for topical application and is absorbed by the skin only after extended rubbing. On the other hand, the cream according to the invention can be rapidly and effectively rubbed in and the patients perceive a rapid onset of drug effect.

TABLE 2

| | | Cream According To the Invention (5%) | | Commercially Available Cream (10%) | |
|---|---|---|---|---|---|
| Number of Patients Exhibiting | | Before the Therapy | After 3 Days of Therapy | Before the Therapy | After 3 Days of Therapy |
| Pain in state of rest* | n.p. | 0 | 0 | 1 | 1 |
| | l. | 0 | 5 | 1 | 4 |
| | m. | 6 | 2 | 5 | 2 |
| | s. | 1 | 0 | 0 | 0 |
| Pain in motion* | n.p. | 0 | 0 | 0 | 0 |
| | l. | 0 | 3 | 0 | 1 |
| | m. | 2 | 4 | 2 | 5 |
| | s. | 5 | 0 | 5 | 1 |
| Pain on compression* | n.p. | 0 | 0 | 0 | 1 |
| | l. | 1 | 3 | 3 | 4 |
| | m. | 5 | 4 | 4 | 2 |
| | s. | 1 | 0 | 0 | 0 |
| Restriction of motion* | n.p. | 0 | 2 | 0 | 2 |
| | l. | 3 | 5 | 5 | 5 |
| | m. | 4 | 0 | 2 | 0 |
| | s. | 0 | 0 | 0 | 0 |
| Firmness of grip** | n. | 0 | 4 | 0 | 3 |
| | l. | 6 | 3 | 6 | 4 |

TABLE 2-continued

| Number of Patients Exhibiting | | Cream According To the Invention (5%) | | Commercially Available Cream (10%) | |
|---|---|---|---|---|---|
| | | Before the Therapy | After 3 Days of Therapy | Before the Therapy | After 3 Days of Therapy |
| | s. | 1 | 0 | 1 | 0 |

Scale of Judgment:
*n.p. not present
l. light
m. moderate
s. strong
**n. not restricted
l. lightly restricted
s. strongly restricted

EXAMPLE IV 2-(4-Isobutylphenyl)-propionic acid Level in Serum

About 6 grams of the cream according to the invention were rubbed into a skin surface area of 20×20 cm. of eight test persons. At specific time intervals, blood was collected and the 2-(4-isobutylphenyl)-propionic acid content was determined. The average values of each determination are represented in FIG. 1. This concentration vs. time graph shows a high rate of absorption of 2-(4-isobutylphenyl)-propionic acid from the cream according to the invention within the first two hours.

As noted above, the amount of the 2-(4-isobutylphenyl)-propionic acid based upon the total weight of the base is from about 2 to about 12 parts by weight. In terms of total dosage, the total amount will vary based upon the illness. As a transdermal analgesic to provide localized pain relief, the amount of 2-(4-isobutylphenyl)-propionic acid on a daily basis is from about 200 to about 400 mg per day. To provide such a dosage, and recognizing that the experimentation set forth above demonstrates both a prompt release of 2-(4-isobutylphenyl)-propionic acid and also a sustained release over a period of at least six hours. The region to be treated is typically given a topical application from three to six times per day with a "cord" of from about 5 to about 10 cm of the cream.

As a transdermal agent for the treatment of localized rheumatism, a dosage of from about 600 to about 3000 mg per day is applied, also typically divided into several applications.

As a transdermal medication for the systemic delivery of 2-(4-isobutylphenyl)-propionic acid, it is recognized that there are known creams that have been proposed but, due to the acicular undissolved 2-(4-isobutylphenyl)-propionic acid that is present in such prior art creams, a lower total amount of 2-(4-isobutylphenyl)-propionic acid is necessary for the essentially fully dissolved forms of the present invention. Indications include degenerative and inflammatory articular diseases, soft tissue rheumatism, lumbago, myogelosis and traumatic athletic injuries. The topical dosage form may also provide therapy in other conditions where 2-(4-isobutylphenyl)-propionic acid is indicated and gastric side effects need to be avoided. When using a pharmaceutical composition according to the invention, lower amounts of 2-(4-isobutylphenyl)-propionic acid as the active ingredient are sufficient than with the use of the creams now commercially available.

What is claimed is:

1. A transdermal medicament for the delivery of 2-(4-isobutylphenyl)-propionic acid to a patient which comprises a sustained release vehicle containing a pharmaceutically effective amount of 2-(4-isobutylphenyl)-propionic acid, said sustained release vehicle comprising a base capable of substantially dissolving all of said 2-(4-isobutylphenyl)-propionic acid and containing from about 30 to about 50 parts by weight $C_{6-12}$ carboxylic acid triglyceride, about 4 to about 10 parts by weight glycerol monostearate-polyoxyethylene stearate mixture and about 2 to about 10 parts by weight polyoxyethylene fatty acid ester.

2. A transdermal medicament cream for the delivery of 2-(4-isobutylphenyl)-propionic acid to a patient which comprises in intimate mixture an aqueous phase mixed with a base containing a pharmaceutically effective amount of 2-(4-isobutylphenyl)-propionic acid in admixture with from about 30 to about 50 parts by weight $C_{6-12}$ carboxylic acid triglyceride, about 4 to about 10 parts by weight glycerol monostearate-polyoxyethylene stearate mixture and from about 2 to about 10 parts by weight polyoxyethylene fatty acid ester.

3. A transdermal medicament of claim 2 wherein said aqueous phase comprises from about 2 to about 10 parts by weight, 1,2-propanediol, about 0.1 to about 1 part by weight 4-hydroxybenzoic acid methyl ester, and from about 0.1 to about 1 part by weight xanthan gum.

4. A method of topically providing an analgesic effect to a patient suffering from a localized pain which comprises topically administering to said patient the transdermal medicament of claim 1, 2 or 3.

5. A method of topically providing an antirheumatic effect to a patient suffering from rheumatism, which comprises topically administering to said patient the transdermal medicament of claim 1, 2 or 3.

6. A method of systemically administering 2-(4-isobutylphenyl)-propionic acid to a patient without a first-pass effect which comprises transdermally administering 2-(4-isobutylphenyl)-propionic acid contained in the transdermal medication of claim 1, 2 or 3, whereby a systemic effect of 2-(4-isobutylphenyl)-propionic acid is delivered to said patient without passage of 2-(4-isobutylphenyl)-propionic acid through the liver of said patient prior to delivery to the bloodstream.

* * * * *

UNITED STATES PATENT AND TRADEMARK OFFICE
CERTIFICATE OF CORRECTION

PATENT NO. : 4,555,524

DATED : November 26, 1985

INVENTOR(S) : Gruber, et al.

It is certified that error appears in the above-identified patent and that said Letters Patent is hereby corrected as shown below:

In the filing date, correct "1981" to read --1982--.

Signed and Sealed this

Thirteenth Day of May 1986

[SEAL]

Attest:

Attesting Officer

DONALD J. QUIGG

Commissioner of Patents and Trademarks